United States Patent
Lancelin et al.

(10) Patent No.: US 7,333,204 B2
(45) Date of Patent: Feb. 19, 2008

(54) METHOD AND DEVICE FOR ANALYSING A GAS LIKELY TO CONTAIN PARTICLES OR SUSPENDED AEROSOLS

(75) Inventors: Henri Lancelin, Morangis (FR); Gilles Guene, Levis Saint Mom (FR); Patrick Bleuse, Le Quesnoy (FR); Pierre Clausin, Ville d'Avray (FR)

(73) Assignee: Proengin SA, Saint Cyr l'Ecole (FR)

( * ) Notice: Subject to any disclaimer, the term of this patent is extended or adjusted under 35 U.S.C. 154(b) by 56 days.

(21) Appl. No.: 10/117,053

(22) Filed: Apr. 8, 2002

(65) Prior Publication Data

US 2002/0145736 A1  Oct. 10, 2002

(30) Foreign Application Priority Data

Apr. 10, 2001 (FR) .................................. 01 04934

(51) Int. Cl.
 G01N 21/00 (2006.01)
 G01N 21/25 (2006.01)
 G01N 31/12 (2006.01)
 G01N 27/00 (2006.01)
 G01J 3/30 (2006.01)

(52) U.S. Cl. ..................... 356/437; 356/315; 356/417; 422/82.05; 422/82.09; 422/91; 422/94; 422/98

(58) Field of Classification Search ........ 356/436–440, 356/73, 315
See application file for complete search history.

(56) References Cited

U.S. PATENT DOCUMENTS 4,730,922 A * 3/1988 Bach et al. ................... 356/73

* cited by examiner

Primary Examiner—Gregory J. Toatley, Jr.
Assistant Examiner—Amanda H Merlino
(74) Attorney, Agent, or Firm—Browdy and Neimark, PLLC

(57) ABSTRACT

The present method uses a spectrophotometric and/or ionisation detection device in which the gas to be analyzed and illuminated by a light source emitting in a range of wavelengths distinct from the one used for spectrophotometry so as to carry out a nephelometric and/or turbidimetric detection, the results of this detection being used to carry out an adjustment of the device for counting the particles and/or for determining the composition of these particles.

8 Claims, 1 Drawing Sheet

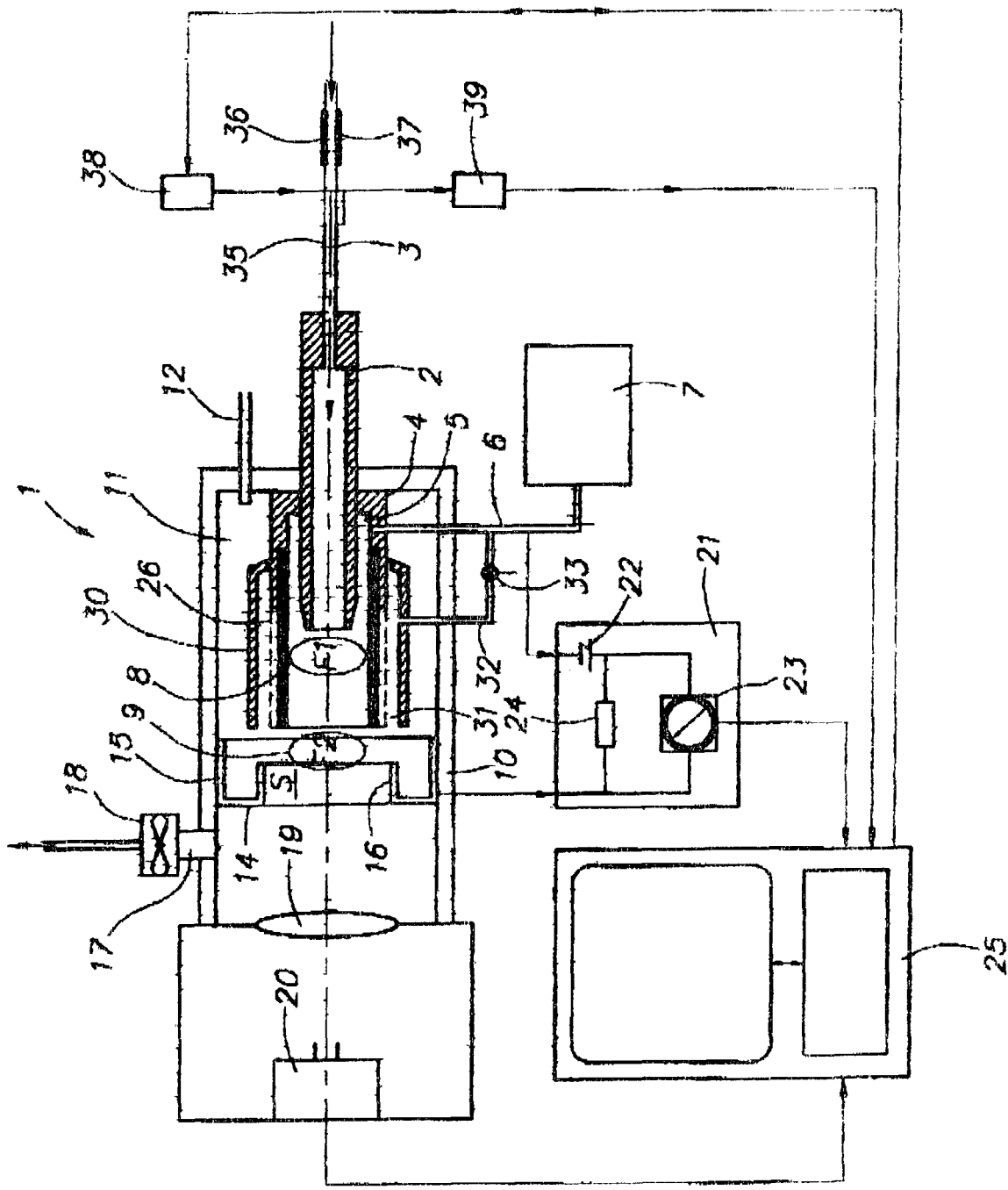

METHOD AND DEVICE FOR ANALYSING A GAS LIKELY TO CONTAIN PARTICLES OR SUSPENDED AEROSOLS

BACKGROUND OF THE INVENTION

1. Field of the Invention

The present invention concerns a device for counting and analysing particles or aerosols suspended in air.

2. Description of the Prior Art

Advantageously not but exclusively, it combines in a device for analysing a gas composition by means of flame spectrophotometry, for example of the type described in the patent FR No. 98 00761 filed in the name of the Applicant.

Generally speaking, it is known that flame spectrophotometry is a method consisting of conducting a spectrographic analysis of the radiation produced by the flame of a gas mixture including the elements to be analyzed and an oxidant gas, such as hydrogen. This analysis is effected by isolating the characteristic radiations of the sought-after elements and by measuring these radiations by photometric means.

So as to be able to apply this method to certain elements which do not generate any characteristic light emission, it is necessary to provoke prior to combustion a reaction of these elements with a reactive element so as to obtain a compound producing an identifiable and detectable light emission.

This prior reaction can be effected out by carrying out a first combustion in the presence of a reactive agent.

The gas mixture derived from this first combustion is subjected to a second combustion which produces a light emission for which the spectrophotometric analysis is also carried out.

This spectrophotometric detection can be associated with a detection of ionisation of the flame by means of electrodes placed in the combustion chamber of the burner. These electrodes are connected to an electronic circuit for measuring the conductivity of the zone where combustion occurs.

This measurement makes it possible to detect the presence of combustible constituents in the sample and in particular organic materials: the combustion of this organic material in fact produces between the measuring electrodes an ionisation current in relation with the organic material concentration.

The information delivered by the spectrophotometric assembly and detection of ionisation can be sent to a processor programmed so as to interpret this information and deduce from it sought-after element concentrations, whether they be compounds, chemical substances or even biological substances (bacteria).

In fact, in the case where the gas sample to be analyzed contains suspended particles, these particles on burning generate light impulses (flash) of limited period which it is possible to count so as to obtain the number of particles per unit of gas volume to be analyzed.

OBJECT OF THE INVENTION

More particularly, the object of the invention is to improve the results of these analyses and countings by extending as much as possible the range of biological substances able to be analyzed.

SUMMARY OF THE INVENTION

To this effect, it concerns illuminating the gas current entering the ionisation and/or spectrophotometric detection device with the aid of a light source emitting according to range of wavelengths not used by the spectrophotometric detector and carry out a nephelometric and/or turbidimetric detection of the illuminated gas stream.

Advantageously, the spectrophotometric detector shall be designed so that the illuminated gas streams flows into the axis of the burner and of the detection optics of the spectrophotometer.

In this case, the light source shall be centered perpendicular to the flow axis of the gas stream: nephelometric detection could use the optics, even indeed the detector of the device carrying out the spectrophotometric measurements.

It is clear that by means of these arrangements, the nephelometric and/or turbidimetric detection makes it possible to detect the presence and size of the particles and/or characteristics able to help in identifying them.

This information is sent to a processor used to carry out adjustments of the spectrophotometer and to process the information detected so as to determine the sought-after element concentrations.

In the presence of a particle selected according to is size, the processor could carry out the required adjustments so as to obtain a maximum of precision during analysis of the luminous radiation produced during moving of this particle into the flame.

Of course, this double detection makes it possible to refine the statistical readings and the deductions which are required to identify the particle.

In particular, this double detection makes it possible to distinguish the humid particles from the dry particles.

BRIEF DESCRIPTION OF THE DRAWINGS

There follows a non-restrictive example of an embodiment of the invention with reference to the accompanying drawings on which:

The sole FIGURE is a skeleton diagram of an analysis device combining flame ionisation, spectrophotometric and turbidimetric measurements and possibly fluorescence measurements.

DESCRIPTION OF THE PREFERRED EMBODIMENTS

In this example, the analysis device includes a tubular burner 1 including a tubular nozzle 2 connected on one side to an intake pipe 3 for the gas to be analyzed, and on the other side and coaxially to this nozzle 2.

A first tubular sleeve 4 having a diameter slightly large than that of the nozzle 2 and axially offset with respect to the latter so as to firstly delimit with the nozzle 2 a first annular intake chamber 5 connected to a hydrogen injection circuit 6 originating from a source 7, and secondly beyond the first nozzle 2 a combustion chamber 8 in which the partial combustion of the gas to be analyzed and the hydrogen generates a first flame $F_1$: this first tubular sleeve 4 is closed on side on the nozzle 2 and opens on the other side into a second combustion chamber 9.

A second tubular sleeve 10 having a diameter larger than that of the first tubular sleeve 4 and delimiting with the latter a second annular intake chamber 11 connected to a circuit 12 for admitting a gas or oxidant gas mixture, such as air; this second sleeve 10 closes on one side on the nozzle 2 and/or on the first sleeve 4 and delimits on the other side beyond the latter the second combustion chamber 9 in which a postcombustion in an oxidant environment of the gases originating from the first combustion chamber 8 and from the intake chamber 11.

an annular electrode 14 having an approximately inverted C-shaped section rendered integral via its face of larger diameter 15 with the second sleeve 10 and whose face of smaller diameter 16 having an axial length smaller than that of the face 15 delimits an outlet pipe S of the combustion chamber 9: beyond the electrode 14 (on the side opposite the sleeve 4), the sleeve 11 includes a lateral orifice 17 into which opens is an exhaust pipe fitted with a turbine activated by a motor;

focusing optics 19, such as a lens mounted in the circular opening of a cover closing the sleeve 10 on the side opposite the nozzle 2, these focusing optics 19 being designed to focus the light radiation emitted in the two combustion chamber 8, 9, in particular the first chamber 8 on the inlet orifice of a spectrophotometric mounting 20.

In this example, the tubular sleeve 4 is made of an electrically conductive material and constitutes a second electrode which cooperates with the electrode 14 so as to allow measurement of the conductivity of the zone of the second chamber 9 in which the second flame extends (flame $F_2$).

These two electrodes are electrically connected to resistor measurement means 21 which include a voltage source 22 mounted in series with a voltmeter 23, this unit being shunted by a resistor 24.

The information delivered by the spectrophotometric mounting 20 and the voltmeter 23 are transmitted to processor/display 25 unit programmed to determine the concentration of elements and or sought-after substances of the gas sample brought be the nozzle 2.

As previously mentioned, the external surface of the sleeve 4 could be covered by a coating 26 made of a suitable material for omitting a reactive gas at the temperature to which this sleeve 4 is brought under the effect of the combustion generated in the first combustion chamber 8. By way of example, this reactive material could consist of indium, the corresponding sought-after elements then being chlorine.

In this case, burner could include a third tubular coaxial sleeve 30 extending into the intercalated space between the sleeves 4 et 10. This third sleeve 30 delimits with the sleeve 4 an annular chamber opening into the second combustion chamber 9 and used for admitting into this chamber 9 of hydrogen current derived from the source 7. To this effect, the annular chamber 31 is connected to the source 7 by means of an intake circuit 32 controlled by a valve 33.

The functioning of the previously described burner is as follows:

Both of the two chambers 8, 9 are placed in a partial vacuum by the turbine 18 so as to provoke a sucking up of the gas to be taken from the nozzle 2 through another nozzle provided in the intake circuit 3

Inside the sleeve 4, the gas stream (for example air) mixes with the hydrogen current injected by the intake chamber 5 in such a proportion that the combustion produced in the first combustion chamber 8 reduces. The light radiation generated by the flame $F_1$ present in the first chamber 8 makes it possible to detect by means of the spectrophotometric mounting 20 compounds, such as phosphorous and sulphur, and deduce from these the presence of the sought-after elements.

The temperature generated by this combustion provokes heating of the sleeve 4 and thus of the coating 26.

When its vaporisation temperature is reached or exceeded, this coating 26 emits a reactive vapour which mixes with the hydrogen flow injected by the intake chamber 31 and with the air derived from the intake chamber 11.

On leaving these chamber 11 and 31, the gas mixture reacts (oxidant combustion) with the gas stream resulting from the partial combustion produced in the chamber 8 so as to produce a flame $F_2$ which emits a light characteristic of a component, such as chlorine, which has reacted with the reactive indium vapour. This light, just like the one produced in the chamber 8, shall be focused by the lens 19 at the inlet of the spectrophotometric mounting 20.

The information delivered by the mounting 20 and the ammeter 23 (which are representative of conductivity variations of the flame (ionisation) present in the second combustion chamber) are sent to the processor 25 which is programmed so as to interpret this information and deduce from this concentrations of sought-after elements, whether these be compounds, chemical substances or even biological substances (bacteria).

Of course, in the case where the gas sample to be analyzed contains suspended particles (for example bacteria or dust), these particles on burning generate light impulses (flash) of limited period which are possible to count so as to obtain the number of particles per unit of gas volume to be analyzed.

In accordance with the invention, the intake pipe 3 for the gas to be analyzed includes a transparent portion 35, made for example of glass or quartz, and preferably having a square or rectangular section so as to have two parallel plane faces 36, 37.

The face 36 of this transparent portion is illuminated in normal incidence by a light source 38 centered perpendicular to the path of the stream of the gas to be analyzed and thus coaxially to the burner and focusing optics 19.

Opposite the source 38 in relation to the transparent portion, an optical sensor 39 is placed and connected to the processor 25. This optional sensor 39 is used for carrying out a turbidimetric of the gas stream.

By means of the special characteristics of the burner and due to the fact of its passage into the transparent portion 35, the gas stream is located in the axis of the focusing optics 19, the spectrophotometric mounting being used to carry out a nephelometric measurement of this gas stream (detection of the light diffused by the particles present in the illuminated gas stream).

To this effect, the wavelength of the radiation emitted by the source 38 is selected (here close to the infrared spectrum) so as to avoid disturbing the photometric measurement carried out be the mounting 20.

The nephelometric analysis gives an estimate of the light diffused by the particles present in the gas flow. It makes it possible to determine low concentrations of substances by means of measurements of variation of the amount of light.

The turbidimetric analysis is able to provide a measurement best adapted when the gas to be analyzed carries a large number of particles.

It is clear that the combining of these measurements makes it possible to determine the parameters (size, weight, humidity . . . ) so as to classify the particles, even before analysing them by means of spectrophotometry.

These two analyses can be possible completed by a fluorescence measurement. In this case, a light source is used functioning in pulsed mode.

The spectrophotometric mounting associated with the burner could possibly be designed so as to carry out in addition the fluorescence spectroscopic examination of the gas flow upstream of the burner.

Of course, the microprocessor 25 shall be programmed so as to make use of the results of all these analyses.

The invention claimed is:

1. A method for analysing a gas flow likely to contain particles or suspended aerosols, said method comprising a step of conducting an analysis of a flame produced in a burner of a spectrophotometric and/or ionisation detection device, said flame being generated by mixing said gas flow with a combustive gas, so as to obtain a combustion, wherein a nephelometric and/or a turbidimetric detection is made of said gas flow by illuminating said gas flow before said combustion with a light source emitting inside a range of wavelengths distinct from one used by said spectrophotometric and/or ionisation detection device so as to obtain information about said particles which are used to adjust said spectrophotometric and/or ionisation detection device and to count said particles, as well as to deduce a composition of said particles on the basis of said information and of information delivered by said spectrophotometric and/or ionisation detection device.

2. Method according to claim 1, which further includes a measurement of fluorescence of the gas flow illuminated by said light source.

3. Method according to claim 2, wherein said light source functions in pulsed mode.

4. Method according to claim 1, wherein said nephelometric measurement is provided by said spectrophotometric and/or ionisation detection device.

5. Apparatus for analysing a gas flow likely to contain particles or suspended aerosol, said device comprising a spectrophotometric and/or ionisation detection device having a burner wherein said gas is injected through an intake pipe and is mixed with a combustive gas so as to produce a flame, and focusing means which focus light radiation emitted by said flame on an inlet orifice of a spectrophotometric mounting, wherein said intake pipe comprises a transparent portion which is illuminated by a light source, and at least one optical sensor is placed in front of said transparent portion so as to cause a turbidimetric and/or nephelometric detection of said flow gas, said optical sensor being connected to a processor which receives information provided from said turbidimetric and/or nephelometric detection, said processor comprising means adjusting said spectrophotometric and/or ionisation detection device and for counting said particles as well as for deducing a composition of said particles on the basis of said information and of information delivered by said spectrophotometric and/or ionisation detection device.

6. Device according to claim 5, wherein a turbidimetric measuring sensor is placed in the axis of the source (38) on the side of the intake pipe opposite the latter.

7. Device according to claim 5, wherein said light source emits in the near infrared spectrum.

8. Device according to claim 5, wherein said spectrophotometric device is designed so as to carry out a nephelometric measurement of the gas flow illuminated by said light source.

* * * * *